(12) United States Patent
Weatherby et al.

(10) Patent No.: US 6,911,534 B2
(45) Date of Patent: *Jun. 28, 2005

(54) METHOD FOR DETERMINATION OF WATER TREATMENT POLYMERS

(75) Inventors: Pauline Weatherby, Manchester (GB); William H. Stimson, Glasgow (GB)

(73) Assignee: Strategic Diagnostics Inc., Newark, DE (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/093,548

(22) Filed: Mar. 8, 2002

(65) Prior Publication Data
US 2002/0127611 A1 Sep. 12, 2002

Related U.S. Application Data

(62) Division of application No. 09/687,503, filed on Oct. 13, 2000, now Pat. No. 6,420,530, which is a continuation of application No. 08/296,272, filed on Aug. 25, 1994, now Pat. No. 6,146,903, which is a continuation of application No. 07/951,963, filed on Sep. 28, 1992, now abandoned.

(30) Foreign Application Priority Data

Feb. 29, 1992 (GB) .............................. 9204409

(51) Int. Cl.$^7$ .................. C07K 16/00; G01N 33/53
(52) U.S. Cl. ................... 530/388.9; 530/389.8; 435/7.1; 435/7.9; 435/7.92; 436/547; 436/548
(58) Field of Search .................. 435/4, 7.1, 7.9, 435/7.92, 7.93, 7.94; 436/547, 548, 39; 530/388.9, 389.8

(56) References Cited

U.S. PATENT DOCUMENTS

| | | | |
|---|---|---|---|
| 4,752,443 A | | 6/1988 | Hoots et al. |
| 4,756,881 A | | 7/1988 | Hoots et al. |
| 5,593,850 A | * | 1/1997 | Wetegrove et al. .......... 436/548 |
| 6,420,530 B1 | * | 7/2002 | Weatherby et al. ...... 530/388.9 |

* cited by examiner

*Primary Examiner*—Padmashri Ponnaluri
*Assistant Examiner*—My-Chau T Tran
(74) *Attorney, Agent, or Firm*—Kilpatrick Stockton LLP

(57) ABSTRACT

A method for determining the presence and/or concentration of a water treatment polymer in an aqueous sample, comprising producing a polyclonal or monoclonal antibody to the water treatment polymer;, and using the antibody so produced as a reagent in an immunoassay, conducted on the aqueous sample.

9 Claims, 1 Drawing Sheet

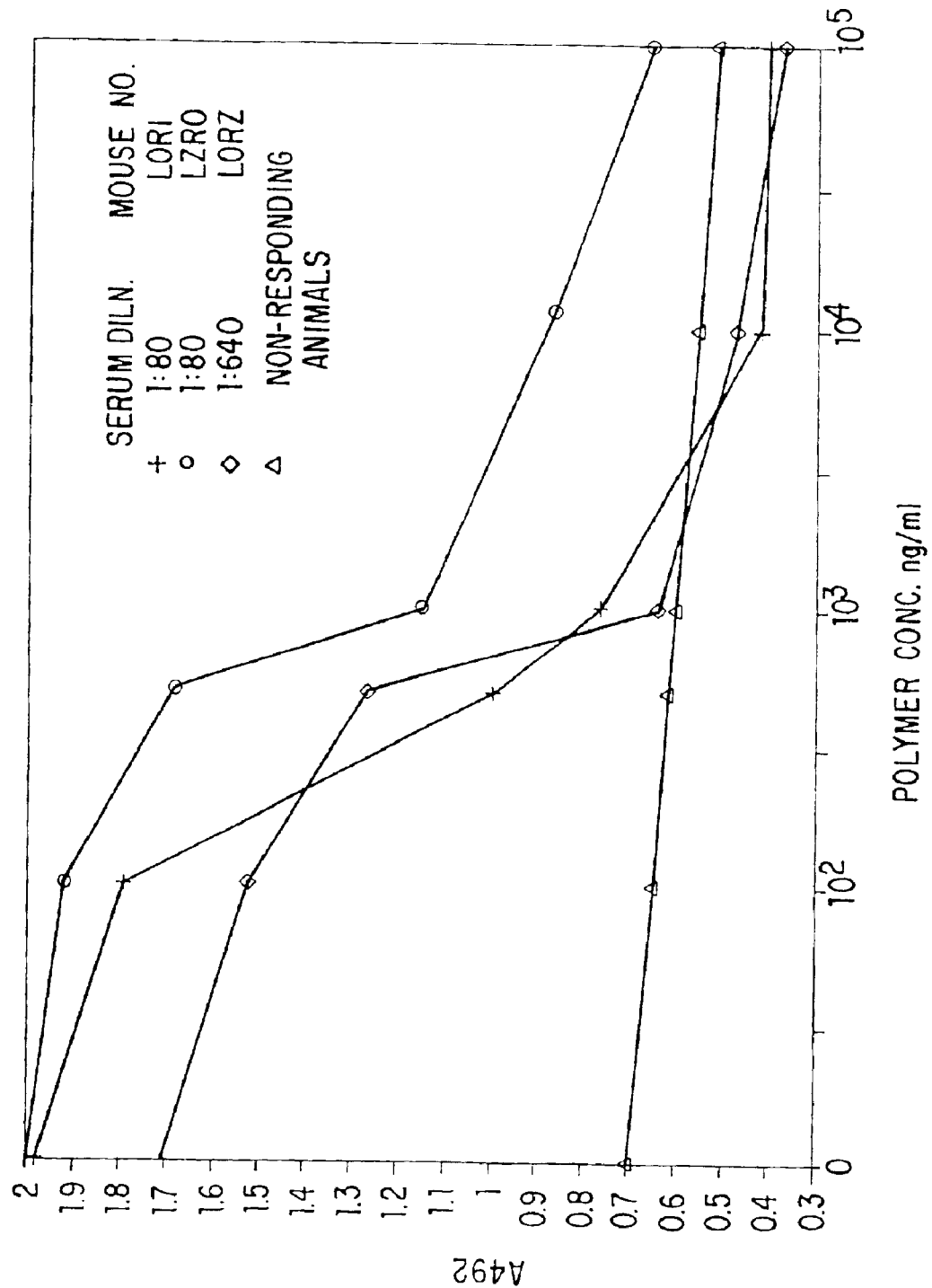

METHOD FOR DETERMINATION OF WATER TREATMENT POLYMERS

This application is a divisional application of U.S. patent application Ser. No. 09/687,503, filed on Oct. 13, 2000, now U.S. Pat. No. 6,420,530, which is a continuation application of Ser. No. 08/296,272, filed on Aug. 25. 1994, now U.S. Pat. No. 6,146,903, which is a continuation application of Ser. No. 07/951,963, filed on Sept. 28, 1992, now abandoned.

The present invention relates to a determination method, in particular to a method, based on immunoassay, for the determination of water treatment chemicals in aqueous media, and to novel antibodies and hybridomas useful in the new method.

The majority of natural waters, and aqueous systems in general, contain dissolved salts of metals such as calcium, magnesium, barium and strontium. When the natural water or aqueous system is heated, the dissolved salts may be converted to insoluble salts, and thereupon deposited as scale on any heat transfer surfaces in contact with the water or aqueous system. Insoluble salt scale may be formed even when the water or aqueous system is merely concentrated, without being heated.

Such precipitation and scale deposition are troublesome and can result in an increase in the costs required to maintain aqueous systems in good working order. Among the problems caused by scale deposits are obstruction of fluid flow, impedance of heat transfer, wear of metal parts, shortening of equipment life, localised corrosion attack, poor corrosion inhibitor performance and unscheduled equipment shutdown. These problems can arise, e.g. in any circulating water system such as those used in oil drilling wells, steam power plants, water desalination plants, reverse osmosis equipment, heat exchange equipment and equipment concerned with the transport of products and by-products in aqueous media, e.g. fly-ash formed during the combustion of coal, in the production of electricity.

A number of additives, notably polycarboxylates, have been provided as effective scale inhibitors for addition to aqueous systems.

Likewise, natural waters and aqueous systems are corrosive towards metals which are in operational contact with them. Consequently, such aqueous systems must be treated with a corrosion inhibitor, e.g. a phosphonate, in order to prevent deterioration of such metals, e.g. pipelines.

Although water treatment chemicals can be effective at very low concentrations, a certain minimum concentration must be maintained if the aqueous system is to operate trouble-free. With the passage of time, loss of the water treatment chemical from the system occurs and replenishment is necessary to avoid the above-mentioned operational problems. On the other hand, use of excess of water treatment chemical increases operational costs. The need to balance treatment, chemical effectiveness and cost has led, therefore, to the development of methods and devices for monitoring the level of water treatment chemicals in aqueous systems.

For example, colourimetric methods are available for the determination of scale inhibitors, e.g. polycarboxylates. Colorimetric methods, however, have the disadvantage that they are subject to interference from extraneous materials. In oil field applications, for instance, interference arises mainly from iron and oil-derived organic materials.

In an attempt to overcome this interference problem, a sample-preparation (pretreatment) cartridge maybe employed, in which interfering species are removed and the water treatment chemical is concentrated. Unfortunately, however, such techniques can result in loss of the water treatment chemical being determined due to competition from the organics for adsorption sites on the cartridge. Such methods are time consuming, lack robustness and the required sensitivity (limits of detection only 1–2 ppm). In addition they require a certain amount of expertise in order to be used effectively to conduct the required determination.

More recently, immunological methods have been developed for the determination of organic compounds.

Immunological methods for determining proteins, cells, hormones, vitamins, drugs and mycotoxins etc. have been known for many years, and have been widely reported in the literature. In such methods, an animal, often a mouse or rabbit, is immunize, either with an analyte or a protein-analyte conjugate. The antibodies produced by the animal are then used, in the form of an immunoassay, to determine the analyte. These methods are based upon the specific reaction between the analyte and the antibody.

The immunoassays which have been reported in the literature incorporate antibodies that have been raised to natural molecules. Recently, however, EP 260829A, has disclosed novel mono- and polyclonal antibodies which are reactive with chlorinated phenols, especially pentachlorophenol. The antibodies can then be used to identify and assay pentachlorophenol, which is widely used as a pesticide and preservative.

We have now succeeded in applying an immunoassay method to the detection of water treatment polymers in aqueous solution, to provide a determination method which is sensitive, specific, rapid, robust and which can be operated by relatively inexperienced personnel—this has not been achieved by such methodology before the present application.

It is surprising that an antibody can be raised effectively to molecules which are polydisperse i.e. having differing molecular weights which vary considerably in size and shape. The competitive assay results demonstrate that the antibodies are raised to the core active centre of the molecules i.e. a moiety which is present in every molecule in the product although the number of repeating monomer units can vary.

Accordingly, the present invention provides a method for determining the presence and/or concentration of a water treatment polymer in an aqueous sample, comprising the production of polyclonal or monoclonal antibody to the water treatment polymer, and using the antibody so produced as a reagent in an immunoassay conducted on the aqueous sample.

The present invention also provides a method for determining the presence and/or concentration of a water treatment polymer in an aqueous sample, comprising an effective amount of a monoclonal antibody or polyclonal antibody which has been raised to the water treatment polymer, in association with an acceptable carrier.

Preferred water treatment polymers, for determination in the process of the present invention, are phosphorus acid containing carboxylic acid telomers having the formula I:

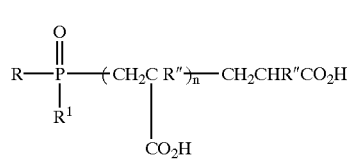

or salts thereof, in which R" is hydrogen, methyl or ethyl, R is hydrogen, $C_1$–$C_{18}$ alkyl, $C_5$–$C_{12}$ cycloalkyl, aryl, aralkyl, a residue of formula:

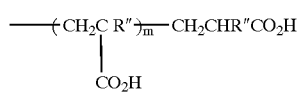

in which R" has its previous significance and the sum of m and n is an integer of at most 100, or R is a residue —OX in which X is hydrogen or $C_1$–$C_4$ alkyl, and $R^1$ is a residue —OX in which X has its previous significance.

The telomers of formula I, and their production are described in more detail in U.S. Pat. No. 4,046,707.

Particularly preferred telomers of formula I are those having the formula IA:

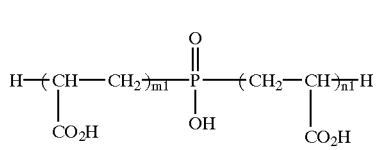

in which the sum of m' and n' is an integer ranging from 4 to 32, especially, 15 to 20.

Other preferred water treatment polymers, for determination in the process of the present invention are hydrolyzed terpolymers of maleic anhydride with other monomers the molar ratio of maleic anhydride to the other monomers ranging from 2.5:1 to 100:1 and the molecular weight of the terpolymer being below 1000. Such terpolymers are described in U.S. Pat. No. 4,126,549.

Preferred ratios of monomers in the terpolymer are in the range of 2½–3½:1 of maleic anhydride to other monomers. Preferred other monomers are vinyl acetate acid and ethyl acrylate.

These ratios are those used in the preparation of the cotelomer of formula II and are not necessarily the ratios to be found in the final cotelomer.

Other examples of preferred water treatment molecules include other polyacrylic acid polymers; copolymers of acrylic acid and acrylamidomethylpropane sulphonic acid (AMPS); copolymers of acrylic acid and vinyl acetate; polymaleic acid; hydrolysed polymaleic acid; terpolymers of maleic acid, ethyl acrylate and vinyl acetate; copolymers of acrylic acid and maleic anhydride; copolymers of maleic acid and sodium allyl sulphonate; and copolymers of maleic anhydride and sulphonated styrene-and vinyl sulphonic acid telomers.

With respect to aqueous systems in which water treatment polymers to be determined may be present, of particular interest are the aqueous systems employed in cooling water plant steam generating plant, sea-water evaporators, reverse osmosis equipment, paper manufacturing equipment, sugar evaporator equipment, soil irrigation plant, hydrostatic cookers, gas scrubbing systems, closed circuit heating systems, aqueous-based refrigeration systems and down-well systems.

The antibody used in the method and composition of the present invention may be produced by known techniques.

For the production of polyclonal antibodies which are reactive with a particular water treatment polymer, firstly an immunogenic conjugate of the polymer and a macromolecule carrier may be produced; an animal may then be immunized with the conjugate, the polymer alone, adjuvant or a discrete mixture of each; blood may be removed from the animal and the serum separated from the blood; and finally the polyclonal antibodies may be recovered from the serum.

It may be preferred, however, to use monoclonal antibodies, which are reactive with specific epitopes on the water treatment polymer, in the method and composition of the present invention, especially in view of their superior specificity for a particular polymer. Monoclonal antibodies may be obtained by the technique first described by Kohler and Milstein, Nature, 265:495 (1975). This technique comprises providing an immunogenic form of the specific water treatment polymer, immunizing an animal with such; obtaining antibody-producing cells from the animal; fusing the cells so obtained with myeloma cells to produce hybridomas; selecting from the hybridomas a hybridoma which produces an antibody which reacts with the specific water treatment polymer, and then isolating the monoclonal antibody from the selected hybridoma.

Water treatment polymers generally have low molecular weights and do not, per se, induce the production of antibodies. They can be used as hapten, however, in combination with a higher molecular weight, immunogenic carrier, such as a protein, using e.g. the technique disclosed by Albro et al. Toxicol Appl. Pharmacol 50,137–146 (1979).

The conjugate so obtained may then be used to immunize an animal host, by conventional techniques, e.g. inoculation. The animal host may be, e.g. a rabbit or a rodent such as a rat or mouse.

After the host animal has produced antibodies to the administered conjugate, polyclonal antibodies may be recovered from the animal by conventional techniques.

For example, blood may be removed from the animal and serum may be separated from the blood so removed. The desired antibodies may then be removed from the serum, e.g. by affinity purification or salt fractionation.

To produce monoclonal antibodies to the water treatment polymer, cells which produce antibodies may be recovered from the immunized animal. B lymphocytes removed from the animal's spleen are preferred.

The removed cells are fused with myeloma cells to produce hybridomas, which are then separated, again using standard techniques such as cloning by limiting dilution.

Once the hybridomas have been separated a selection is made to ascertain those which produce antibodies to the specific water treatment polymer to be determined in the method of the present invention. The relevant specific hybridomas can then be isolated by known methods, and the relevant antibodies secreted from them by conventional techniques.

The following examples further illustrate the present invention.

EXAMPLE 1

1. Preparation of Protein Conjugates

A telomer (Telomer 1) derived from 16 moles of acrylic acid and 1 mole of hypophosphorous acid and produced by the method of U.S. Pat. No. 4,046,707 is bound to a carrier protein keyhole limpet haemocyanin (KLH) using 1-ethyl-3-(3-dimethylaminopropyl)-carbodiimide hydrochloride (EDC). In addition the product is bound to a second protein, ovalbumin (OVA) for screening purposes.

Essentially 2 mg of KLH or OVA are dissolved with 200 $\mu$l of deionized water. In addition, 2 mg of the peptide to be coupled are dissolved in 0.5 ml of conjugation buffer (0.1M (2-(N-morpholino)-ethanesulfonic acid) MES, 0.9M sodium chloride NaCl and 0.02% sodium azide $NaN_3$, pH 4.7).

The 500 $\mu$l of peptide solution are added to the 200 $\mu$l of carrier protein solution. For OVA conjugation, this solution is added to 10 mg of EDC and dissolved by gentle mixing. For KLH conjugation, the 10 mg of EDC are dissolved in 1 ml of deionized water and 50 $\mu$l of this solution are added immediately to the carrier—peptide solution.

The reaction proceeds for 2 hours at room temperature. Any precipitate is removed using centrifugation prior to purification.

The conjugate is purified using gel filtration or Sephadex G50 (0.5×5 cm). The column is washed using 5 ml of phosphate buffered saline PBS. The peptide carrier mixture is applied directly to the top of the column and the eluate collected. 0.5 ml aliquots of PBS are added and each fraction is collected in a separate tube. 15 mls of PBS are added to elute both the conjugate and the peptide. The immunogen elutes between fractions 4–6, and the free peptide and reagents after fraction 8.

The hapten—carrier ratios are determined spectrophotometically and by assessment of the concentrations of the reactants following conjugation. The molar ratio of polymer per 100,000 mol. wt of carrier is 6–11.

2. Immunisation of Animals a) Mice (NZB/NZW F1 hybrid females and BALB-c females), 6–8 weeks old, receive 0.2 mg polymer in 0.1 ml 0.15M NaCl solution (saline) mixed with 0.1 ml Freunds complete adjuvant (FCA) and 100 $\mu$g polymer conjugate (by protein concentration) in 0.1 ml saline. Thereafter animals are injected every 18–21 days with the same antigen preparations and doses except that Freunds incomplete adjuvant (FIA) is substituted for FCA. All injections are intraperitoneal and animals sacrificed for blood or spleens.

b) Rats (Sprague-Dawley females) aged 12–16 weeks are injected with the identical protocol indicated in (2a). Blood is obtained by heart puncture.

c) Rabbits (NZW-female) aged 4 months, are injected as follows—day 0, intramuscular; day 14, intramuscular, day 24 intraperitoneal. All treatments contain 50 ug protein or 200 ug polymer/0.2 ml and are given in conjunction with 0.2 ml FCA (day 0), 0.2 ml FIA (day 14), 0.2 ml saline (day 24). Blood is obtained on day 34 by venepuncture, allowed to clot at room temperature and the serum separated by centrifugation (2000 g, 15 min, 4° C).

3. Monclonal Antibody Production

Mice, immunised as indicated above, are injected with polymer or conjugate (at the doses shown in 2a) 3 days prior to sacrifice.

The spleens are removed and the splenocytes isolated by dissection into Hanks Balanced Salt Solution. These spleen cells are fused with cells from the X63.Ag 8 6.5.3 murine myeloma line, in exponential growth, in a ratio of 4:1 by the addition of 1 ml 46% (w/v) polyethylene glycol 1550 (Serva) in RPMI 1640 with gentle mixing for 3 min at 37° C. After standing for 2 min at room temperature, the mixture is slowly diluted by the drop-wise addition of 20 ml RPMI 1640 over 5 min, followed by standing at room temperature for 10 min. After washing twice with RPMI 1640, the cells are incubated for 2 hr at 37° C. in bicarbonate-buffered RPMI 1640, supplemented with 10% (v/v) fetal calf serum, 2 mmol/l L-glutamine, 50 IU/ml penicillin and 50 ug/ml streptomycin (Flow) and containing $1 \times 10^{-4}$ mol/l hypoxanthine and $1.6 \times 10^{-5}$ mol/l thymidine (HT medium). The cell suspensions (100 ul) are then dispensed into 96-well tissue culture plates (Costar) at three different concentrations (2.5, 1.25 and $6 \times 10^6$ cells/ml). Finally, 200 ul HT medium containing $4 \times 10^{-7}$ mol/l aminopterin (HAT medium) are added to each well. The plates are incubated at 37° C. in a humidified atmosphere of 5% $CO_2$ in air. Hybridoma cells are initially grown in HAT medium but this is eliminated after 14 days by step-wise replacement with HT medium. Supernatant liquids are screened for specific antibody by indirect non-competitive ELISA 14–18 d post-fusion. Specific hybridomas are subsequently expanded into flasks and cloned three times or until 100% cloning efficiency is obtained. This procedure is carried out by limiting dilutions in 96-well tissue culture plates containing a feeder layer of spleen cells ($2 \times 10^5$ cells/well) from non-immunized NZB/DALB-C hybrid mice. Cell lines of interest are maintain in vitro in culture medium and are frozen, at a concentration of $5 \times 10^6$ cells/ml, in RPMI 1640 containing 30% bovine serum and 15% dimethyl sulphoxide (Sigma) and stored in liquid nitrogen (Islam, M. S. and Stimson, W. H. Lett. Appld. Microbiol., 4, 85–89 (1987).

4. ELISA Procedures a) Indirect non-competitive ELISA—for screening hybridoma supernatants and sera from animals for the presence of antipolymer antibodies.

i) Flat-bottomed 96-well microtire plates (Dynatech) are coated with polymer conjugate—10 ug protein/1 ml 0.02M Tris/HCl buffer, pH 9.0. Aliquots (100 ul per well) are distributed into microliter plates and incubated for 1 h at 37° C. The solution is then removed and replaced with 100 ul 1% (w/v) BSA solution in 0.02M Tris/HCl, pH 9.0, for 30 min at 37° C. Thereafter, the plates are washed (×4) with 0.2M Tris/HCl buffer pH 7.4 containing 0.2M NaCl and 0.05% (v/v) Tween 20 (wash buffer). These plates may be dried in vaccuo and stored dry for up to one year or used immediately for assays.

ii) Hybridoma supernatants or animal sera (dilutions 1:10 to $1:10^5$ commonly) are added to the plates—100 ul per well. Following incubation for 45 min, 37° C. the plates are washed ×3 with wash buffer.

iii) Sheep anti-mouse $\gamma$-globulins—horse radish peroxidase conjugate (SAPU, Carluke, Scotland) is diluted 1:2000 in 0.15M NaCl containing 25% (v/v) sheep serum. Aliquots (100 ul) are added to each well and incubated for 45 min at 37° C. before washing ×3 with wash buffer. Enzymic activity (A450) is measured with 200 ul tetramethylbenzidine substrate, pH 5.5, the reaction is stopped ater 30 min, room temperature with 50 ul 2M $H_2SO_4$.

b) Sandwich ELISA—for estimating polymer concentrations in samples.

i) Antisera are precipitated with $(NH_4)_2SO_4$ solution and redissolved in 0.15M NaCl solution to give a concentration of 15 mg/ml. This is diluted in 0.02M Tris/HCl, pH 9.0 from 1:500 to 10,000 and used to coat microliter plate wells (100 ul per well) for 1 h at 37° C. The plate is washed ×5 with wash buffer before use.

ii) Polymer standards (10 ng/ml to 20 ug/ml) 0.15M NaCl solution and samples (100 ul) are added to wells for 45 min at 37° C. The plate is washed ×3 in each buffer.

iii) Antibody/antiserum—enzyme conjugate preparation is achieved by periodate coupling of horse radish peroxidase (HRP).

5 mg of HRP is resuspended in 1.2 ml of water. 0.3 ml of freshly prepared 0.1M sodium periodate in 10 mM sodium phosphate (pH 7.0) is added.

The solution is incubated at room temperature for 20 min prior to dialysing the HRP solution versus 1 mM sodium acetate (pH 4.0) at 4° C. with several changes overnight.

An antibody solution of 10 mg/ml in 20 mM carbonate (pH 9.5) is prepared.

The HRP is removed from the dialysis tubing and added to 0.5 ml of the antibody solution and is incubated at room temperature for 2 hr.

The Schiff's bases, thus formed, are reduced by adding 100 ul of sodium borohydride (4 mg/ml in water) and incubated at 4° C. for 2 hr.

The solution is dialyzed versus several changes of PBS.

iv) Antibody-enzyme conjugate (100 ul) prepared as in (iii) and diluted 1:500 to 1:300,00 is added and reaction/readings taken as in [4a(iii)].

c) Competition ELISA i) As for [4a(i)].

ii) Compounds/samples (100 ul) are added to wells and simultaneously 100 ul antibody-enzyme conjugate is added [see 4b (iii+iv)]. The plate is incubated for 45 min at 37° C. and the procedure described in [4a (iii)] carried out.

The results of this procedure are shown in FIG. 1.

RESULTS

Competition assays are performed to detect the free product in a real aqueous sample. OVA conjugate is bound to the walls of microtitration wells and incubated with 1) Polyclonal antiserum raised to the free form (dilution 1:100 to 1:8000) and free product; range 10 ng/ml to 100 μg/ml (c.f. FIG. 1).
2) Polyclonal antiserum raised to the KLH conjugate (dilution 1:100 to 1:35,000) and free product range 10 ng/ml to 100 μg/ml.
3) Monoclonal antibodies raised to the free form (dilution 1:10$^4$ to 1:10$^6$) and free product range 10 ng/ml to 100 μg/ml and
4) Monoclonal antibodies raised to the KLH conjugate (dilution 1:10$^4$ to 1:10$^6$) and free product range 10 ng/ml to 100 μg/ml.

Assays incorporating polyclonal or monoclonal antibodies to the conjugated form are sensitive only down to 10 μg/ml. Those incorporating polyclonal and monoclonal antibodies to the free form are sensitive down to 0.1 μg/ml (c.f. FIG. 1).

Matrix Interference

The product is prepared in a variety of synthetic waters and two examples of typical north sea formation water in which the product is commonly applied, to determine matrix interference (see Table 1).

Absorbance (A450) of the positive polymer control in the presence of distilled water is 1.68±0.19 AU.

A450 of the negative polymer control is 0.08±0.04 AU.

A450 in the presence of the synthetic waters and one of the north sea formation waters was >1.58±0.28 AU. The second formation water brought about a colour change when added to the tetramethylbenzidine substrate.

TABLE 1

| TYPE | COMPOSITION |
|---|---|
| FORMATION 1 | Barium (Ba$^{2+}$) 1050 ppm |
| | Calcium (Ca$^{2+}$) 1060 ppm |
| | Magnesium (Mg$^{2+}$) 113 ppm |
| | Sodium (Na$^+$) 27,986 ppm |
| | Chloride (Cl$^-$) 43,196 ppm |
| | Potassium (K$^+$) 3833 ppm |
| | Strontium (Sr$^{2+}$) 110 ppm |
| SEAWATER 1 | Sulphate (SO$_4^{2-}$) 2426 ppm |
| | Sodium (Na$^{2-}$) 22,135 ppm |
| | Chloride (Cl$^-$) 34,165 ppm |
| | Potassium (K$^+$) 775 ppm |
| | Bicarbonate (HCO$_3^-$) 497 ppm |
| | THESE ARE MIXED 50/50 or 40/60 OF FORMATION 1/SEAWATER 1 and pH adjusted to 4.5 |
| FORMATION 2 | Barium (Ba$^{2+}$) 252 ppm |
| | Calcium (Ca$^{2+}$) 3523 ppm |
| | Magnesium (Mg$^{2+}$) 1813 ppm |
| | Sodium (Na$^+$) 17,692 ppm |
| | Chloride (Cl$^-$) 39,599 ppm |
| | Strontium (Sr$^{2+}$) 669 ppm |

TABLE 1-continued

| TYPE | COMPOSITION |
|---|---|
| SEAWATER 2 | Sulphate (SO$_4^{2+}$) 2426 ppm |
| | Sodium (Na$^{2-}$) 22,135 ppm |
| | Chloride (Cl$^-$) 34,165 ppm |
| | Potassium (K$^+$) 775 ppm |
| | Bicarbonate (HCO$_3^-$) 497 ppm |
| | THESE ARE MIXED 50/50 OF FORMATION 2/SEAWATER 2 |
| FORMATION 3 | Calcium (Ca$^{2+}$) 467 ppm |
| | Magnesium (Mg$^{2+}$) 75 ppm |
| | Potassium (K$^+$) 377 ppm |
| | Strontium (Sr$^{2+}$) 67 ppm |
| | Barium (Ba$^{2+}$) 65 ppm |
| | Sodium (Na$^+$) 12,932 ppm |
| | Chloride (Cl$^-$) 20,853 ppm |
| SEAWATER 3 | Bicarbonate (HCO$_3^-$) 4000 ppm |
| | Sodium (Na$^+$) 1,511 ppm |
| | THESE ARE MIXED 75/25 OF FORMATION 3/SEAWATER 3 |
| SOLUTION 4 | Calcium (Cl$^{2+}$) 150 ppm |
| | Magnesium (Mg$^{2+}$) 44 ppm |
| | Chloride (Cl$^-$) 199 ppm |
| | Sodium (Na$^+$) 121 ppm |
| | Carbonate (CO$_3^{2-}$) 51ppm |
| | Bicarbonate (HCO$_3^-$) 269 ppm |
| SOLUTION 5 | Calcium (Ca$^{2+}$) 300 ppm |
| | Magnesium (Mg$^{2+}$) 88 ppm |
| | Chloride (Cl$^-$) 398 ppm |
| | Sodium (Na$^=$) 242 ppm |
| | Carbonate (CO$_3^{2+}$) 102 ppm |
| | Bicarbonate (HCO$_3^-$) 538 ppm |
| SOLUTION 6 | Calcium (Ca$^{2+}$) 20 ppm |
| | Magnesium(Mg$^{2+}$) 6 ppm |
| | Chloride (Cl$^-$) 30 ppm |
| | Sulphate (SO$_4$) 21 ppm |
| | Bicarbonate (HCO$_3^-$) 18 ppm |
| | Sodium (Na$^-$) 46 ppm |
| SOLUTION 7 | Calcium (Ca$^{2+}$) 60 ppm |
| | Magnesium (Mg$^{2+}$) 18 ppm |
| | Chloride (Cl$^-$) 200 ppm |
| | Sulphate (SO$_4$) 200 ppm |
| | Bicarbonate (HCO$_3^-$) 427 ppm |
| | Sodium (Na$^+$) 83 ppm |
| SOLUTION 8 | Calcium (Ca$^{2+}$) 400 ppm |
| | Magnesium (Mg$^{2+}$) 1202 ppm |
| | Chloride (Cl$^-$) 18711 ppm |
| | Sodium (Na$^+$) 10522 ppm |
| | Carbonate (CO$_3^{2-}$) 184 ppm |
| | Sulphate (SO$_4^{2-}$) 2623 ppm |
| | Potassium (K$^+$) 395 |
| SOLUTION 9 | Calcium (Ca$^{2+}$) 172 ppm |
| | Sodium (Na$^+$) 304 ppm |
| | Carbonate (CO$_3^{2+}$) 153 ppm |
| | Bicarbonate (HCO$_3^-$) 129 ppm |
| | Chloride (Cl$^-$) 400 ppm |
| | Sulphate (SO$_4^{2-}$) 159 ppm |
| SOLUTION 10 | Calcium (Ca$^{2+}$) 100 ppm |
| | Magnesium (Mg$^{2+}$) 20 ppm |
| | Chloride (Cl$^-$) 118 ppm |
| | Sodium (Na$^+$) 50046 |
| | Hydroxide (OH$^-$) 36167 |
| | Carbonate (CO$_3^{2-}$) 10556 |
| | Potassium (K$^+$) 2422 |
| SOLUTION 11 | Calcium (Ca$^{2+}$) 23 ppm |
| | Magnesium (Mg$^{2+}$) 10 ppm |
| | Silica (SiO$_2$) 28 ppm |
| | Carbonate (CO$_3^{2+}$) 226 ppm |
| | Phosphate (PO$_4^{2-}$) 74 ppm |
| | Iron (Fe$^{3+}$) 34 ppm |
| SOLUTION 12 | Typical natural sea Water sample |
| SOLUTION 13 | Typical north sea formation water Example 1 |
| SOLUTION 14 | Typical north sea formation water Example 2 |

EXAMPLES 2 TO 26

The following compounds of similar structure are substituted in the competion assay, in place of the free product, in the procedure described in Example 1. The results as shown in Table 2 are expressed as a percentage ratio of the mass of polymer giving 50% maximum absorbance to mass of compound of similar structure. The antibody is specific for the determination of phosphinocarboxylic acids.

TABLE 2

| EXAMPLE | COMPOUND | PERCENT CROSS REACTIVITY WITH TELOMER 1 |
|---|---|---|
| 2 | ACRYLIC/ACRYLAMIDE METHYL PROPANOSULPHONIC ACID (AMPS) COPOLYMER 1 | 2.6 |
| 3 | PHOSPHONIC CARBOXYLIC ACID PCA | 105 |
| 4 | PHOSPHONO CARBOXYLIC ACID | 12.3 |
| 5 | ACRYLIC/AMPS COPOLYMER 2 | 9.7 |
| 6 | POLYACRYLIC ACID 1 | 5.4 |
| 7 | POLYACRYLIC ACID 2 | 8.8 |
| 8 | POLYACRYLIC ACID 3 | 10.5 |
| 9 | ACRYLIC COPOLYMER | 22.7 |
| 10 | POLYACRYLIC ACID 4 | 14.4 |
| 1 | ACRYLIC/AMPS COPOLYMER 3 | 12.7 |
| 12 | ACRYLIC/AMPS/POLYETHYLENEGLYCOL COPOLYMER | 9.6 |
| 13 | POLYACRYLIC ACID 5 | 6.6 |
| 14 | 1-HYDROXY ETHYLIDENE-1-1-DIPHOSPHINIC ACID (HEDP)/AMPS COPOLYMER/POLYACRYLIC ACID | 11.4 |
| 15 | PHOSPHONO BUTANE TRICARBOXYLIC ACID (PBTC) | 8.8 |
| 16 | HEDP | 2.1 |
| 17 | PHOSPHONATE 1 | 2.6 |
| 18 | PCA 2 | 91.5 |
| 19 | POLYACRYLIC ACID 6 | 3.0 |
| 20 | PHOSPHONATE 2 | 8.4 |
| 21 | PHOSPHONATE 3 | 9.7 |
| 22 | AMINE OXIDE OF AMINE PHOSPHONATE 1 | 15.6 |
| 23 | AMINE OXIDE OF AMINE PHOSPHONATE 2 | 11.0 |
| 24 | HYDROXYPHOSPHINOUS CARBOXYLIC ACID | 28.2 |
| 25 | ACRYLIC/AMPS COPOLYMER 4 | 11.5 |
| 26 | ACRYLIC/AMPS COPOLYMER 5 | 7.7 |

EXAMPLE 27

Attempts to conjugate the telomer derived from 3 moles of maleic acid 1 mole of vinyl acetate and 1 mole of ethylacrylate with KLH resulted in total precipitation at all reasonable ratios of reactants, as described in Example 1. Low ratio coupling of the product to OVA with EDC is successful (1:4, by weight). In addition low ratio coupling to a second protein, bovine serum albumin (BSA) for screening purposes is also prepared.

Mice and rabbits are immunised as described in Example 1. Antibody production is determined after immobilisation of the second BSA-conjugate onto the walls of a microtitration well and the procedure described in Example 1 is performed.

The conjugated form of the product is shown to be immunogenic. No response is detected from the free form. This is consistent with the size of the molecule being too small ($m_w$<1000 daltons) to stimulate the immune system.

What is claimed is:

1. A method for determining the presence and/or concentration of a polydisperse water treatment polymer in an aqueous sample, comprising (a) contacting a composition comprising an effective amount of a monoclonal or polyclonal antibody which binds to the water treatment polymer wherein the water treatment polymer is selected from the group consisting of a polymaleic acid polymer; a hydrolysed maleic acid polymer; terpolymers of maleic anhydride, ethyl acrylate and vinyl acetate; copolymers of acrylic acid and maleic anhydride; copolymers of maleic acid and sodium allyl sulphonate; copolymers of maleic anhydride and sulphonated styrene; and combinations thereof, with the aqueous sample; (b) incubating the sample with the composition comprising the antibody for a time effective for the antibody to bind to the water treatment polymer to form a complex; and (c) detecting the complex and thereby determining the presence and/or concentration of the water treatment polymer in the aqueous sample.

2. The method of claim 1, wherein the aqueous sample is taken from water employed in plant cooling, steam generating plants, sea-water evaporators, reverse osmosis equipment, paper manufacturing equipment, sugar evaporator equipment, soil irrigation plants, hydrostatic cookers, gas scrubbing systems, closed circuit heating systems, aqueous-based refrigerator systems or down-well systems.

3. The method of claim 1 wherein the water treatment polymer is polymaleic acid polymer or hydrolyzed maleic acid polymer.

4. The method of claim 1 wherein the water treatment polymer is a terpolymer of maleic acid, ethyl acrylate and vinyl acetate.

5. The method of claim 1 wherein the water treatment polymer is a copolymer of acrylic acid and maleic acid.

6. The method of claim 1 wherein the water treatment polymer is a copolymer of maleic acid and sodium allyl sulphonate.

7. The method of claim 1 wherein the water treatment polymer is a copolymer of maleic anhydride and sulphonated styrene.

8. The method of claim 4, wherein the terpolymer comprises a weight of less than about 1000 Daltons.

9. The method of claim 4, wherein the ratio of maleic anhydride to ethyl acrylate or vinyl acetate is from about 2.5:1 to about 100:1.

* * * * *